United States Patent [19]
Gelb

[11] Patent Number: 5,550,984
[45] Date of Patent: Aug. 27, 1996

[54] SECURITY SYSTEM FOR PREVENTING UNAUTHORIZED COMMUNICATIONS BETWEEN NETWORKS BY TRANSLATING COMMUNICATIONS RECEIVED IN IP PROTOCOL TO NON-IP PROTOCOL TO REMOVE ADDRESS AND ROUTING SERVICES INFORMATION

[75] Inventor: Edward J. Gelb, Wayne, N.J.

[73] Assignee: Matsushita Electric Corporation of America, Secaucus, N.J.

[21] Appl. No.: 350,541

[22] Filed: Dec. 7, 1994

[51] Int. Cl.⁶ .................................................... G06F 13/00
[52] U.S. Cl. ...................... 395/200.17; 395/187.01; 370/94.1; 380/49; 364/222.2; 364/222.5; 364/284.3; 364/DIG. 1
[58] Field of Search .............................. 395/200, 200.01, 395/200.10, 200.13, 200.16, 200.17, 187.01; 370/94.1, 60; 380/4, 23, 49

[56] References Cited

U.S. PATENT DOCUMENTS

| | | | |
|---|---|---|---|
| 4,058,672 | 11/1977 | Crager et al. | 178/3 |
| 4,157,454 | 6/1979 | Becker | 380/37 |
| 4,447,871 | 5/1984 | Terada et al. | 395/200.2 |
| 4,476,347 | 10/1984 | Hagen et al. | 178/3 |
| 4,672,572 | 6/1987 | Alsberg | 380/23 |
| 4,799,153 | 1/1989 | Hann et al. | 380/25 |
| 4,924,513 | 5/1990 | Herbison et al. | 380/21 |
| 4,944,006 | 7/1990 | Citta et al. | 380/20 |
| 5,021,949 | 6/1991 | Morten et al. | 370/94.1 |
| 5,081,678 | 1/1992 | Kaufman et al. | 380/21 |
| 5,086,469 | 2/1992 | Gupta et al. | 380/48 |
| 5,105,424 | 4/1992 | Flaig et al. | 370/94.1 |
| 5,113,499 | 5/1992 | Ankney et al. | 395/726 |
| 5,163,151 | 11/1992 | Bronikowski et al. | 395/185.1 |
| 5,216,670 | 6/1993 | Ofek et al. | 370/85.14 |
| 5,249,292 | 9/1993 | Chiappa | 395/650 |
| 5,278,955 | 1/1994 | Forte et al. | 395/200.01 |
| 5,280,581 | 1/1994 | Bathrick et al. | 395/200.09 |
| 5,293,379 | 3/1994 | Carr | 370/94.1 |
| 5,303,303 | 4/1994 | White | 380/49 |
| 5,307,465 | 4/1994 | Iki | 395/311 |
| 5,311,593 | 5/1994 | Carmi | 380/23 |
| 5,321,695 | 6/1994 | Faulk, Jr. | 370/94.1 |
| 5,353,283 | 10/1994 | Tsuchiya | 370/60 |
| 5,416,842 | 5/1995 | Aziz | 380/30 |
| 5,432,850 | 7/1995 | Rothenberg | 380/23 |

OTHER PUBLICATIONS

"Network Firewalls", by Bellovin et al., IEEE Communications Magazine, Sep. 1994, pp. 50–57.

*Primary Examiner*—Thomas C. Lee
*Assistant Examiner*—Moustafa Mohamed Meky
*Attorney, Agent, or Firm*—Amster, Rothstein & Ebenstein

[57] ABSTRACT

A security system for connecting a first computer network to a second computer network is provided. The security device has a pair of computer motherboards, each of which has a network interface adapter for receiving and transferring communications from a computer network to a transfer adapter to be transmitted to the other computer network through a transfer adapter and network interface adapter provided on the other computer motherboard. Each motherboard provides protocol translation from a first protocol to a second protocol and removes source and destination address information from communications transferred to the other computer motherboard. Application program interface shim software or dynamic link library software provides control of communications between the two motherboards for passing code necessary to request and receive services from the other computer network.

13 Claims, 1 Drawing Sheet

SECURITY SYSTEM FOR PREVENTING UNAUTHORIZED COMMUNICATIONS BETWEEN NETWORKS BY TRANSLATING COMMUNICATIONS RECEIVED IN IP PROTOCOL TO NON-IP PROTOCOL TO REMOVE ADDRESS AND ROUTING SERVICES INFORMATION

FIELD OF THE INVENTION

The present invention relates to a security system for preventing unauthorized communications between one computer network and another computer network and more specifically for preventing unauthorized access to a private computer network from a public computer network such as the Internet.

BACKGROUND OF THE INVENTION

Recent developments in technology have made access easier to publicly available computer networks, such as the Internet. The exchange of information between private computer networks and users attached to the Internet presents a challenge to protect information located on such private networks from unauthorized access by outside Internet users, and from unauthorized export by private users to the outside. For example, a group of private users who work for the same entity may need to have access to common data but desire to shield such information from disclosure to outsiders. Recently, accounts have publicized the vulnerability of even the Pentagon's computer system to break-ins by public Internet users known as "crackers." In breaking into private computer networks, crackers have been able to erase files or disks, cancel programs, retrieve sensitive information and even introduce computer viruses, Trojan horses and/or worms into those private networks.

Another related problem is security among related private computer networks. For example, many companies have branches located in various parts of the country. Each branch may contain a computer network and each of these local computer networks are interconnected in a company-wide computer network. It is desirable in the use of such computer networks to prevent unauthorized access to one of the local computer networks from another of the local computer networks.

For communication on the Internet, the protocol suite Transmission Control Protocol/Internet Protocol (TCP/IP) provides a standardized communication format between nodes on a computer network and between computer networks. This protocol suite is used inside and among private computer networks, as well. Private computer networks are often linked to other private computer networks, such as in a company where multiple user groups exist in the organization with corresponding multiple computer networks. The risk of break-ins and computer misuse by one such private network by users of another private network is also present. For example, a disgruntled employee working from a local area network (LAN) in one organization of the company may break into the private computer network of another organization with the company and cause files to be altered or erased or place viruses, Trojan horses, or worms into nodes contained in that network.

Private computer networks come in all forms and are put to many purposes. There are credit card computer networks which direct network traffic to banks for authorizations and transaction posting, there are university computer networks which maintain student or scientific research information, and there are private company computer networks which contain a variety of proprietary information. The future promises to bring even more connectivity to computer networks through such mechanisms as computerized home television and multimedia services. Providing a security system against breach by so-called crackers will be equally important to the home computer user.

Presently known security systems have often proven either to be ineffective in preventing breach of the private computer network, or have severely limited access to communication services for communicating with other networks. In general, existing security systems disable certain critical communication services between the computer networks. For example, in connection with the Internet, such important communications services as file transfer applications such as File Transfer Protocol (FTP), Trivial File Transfer Protocol (TFTP), and HTTP, and terminal emulation services such as Telnet applications have been disabled for the sake of security. However, when such services are disabled, most of the power to communicate with other computer networks is lost, leaving the private network with only basic electronic mail (E-mail) services to the public Internet, such as provided by Simple Mail Transfer Protocol (SMTP) and POP3 applications. Even with such file transfer and emulation services disabled, private networks have not been immune to breach by crackers from the public Internet or other private networks. An outsider can obtain headers from the sendmail and postscript files used in E-mail, including critical data, to enable entrance into privileged files by mimicking a legitimate user.

Such security systems have been implemented in several ways. For example, screening routers have been used to limit transmission into and out of a private network to specific sites or to specific types of transmissions. However, these limitations by their nature also severely restrict access to communication services with the public Internet or other networks.

Host-based firewalls, also known as dual-homed firewalls, provide an additional level of security by interposing a separate computer system between the private network and the public Internet network. In some dual-homed firewalls, Internet Protocol (IP) packet forwarding is disabled, preventing the firewall from routing IP packets automatically according to the addresses provided. Such dual-homed firewalls also provide a special set of Transmission Control Protocol (TCP) applications to act as proxy agents to communicate with users outside of the private network. In this way, the firewall maintains control over the communications which enter and exit the private network. For example, a user on the private network may use an application such as Telnet to log on to the host-based firewall system. The private network user is then prompted for the Internet address of the end-point. The firewall then sets up a pipe between the private network user and the end-point and monitors the connection between the points. A disadvantage identified with host-based firewalls has been the continual need to increase the size of the firewall system to support increased traffic between the private network and the public Internet network. Another disadvantage of host-based firewalls is that crackers need only to overcome the security defenses of a single computer system in order to gain access to the private network.

Another firewall system is known as bastion hosts, also known as an application level firewall, overcomes these disadvantages of host-based firewalls by providing a subnetwork of hosts to control traffic in and out of the private network. The subnetwork can be expanded by adding hosts as capacity need increases. With bastion hosts the public network is permitted to access only up to an exterior router R2, while the private network is permitted to access only up to an interior router R1. Between the routers a group of proxy hosts are provided which control access to various applications available for communication with the private and public networks. A disadvantage of this system is that code must be specially written to specify each application to be allowed through the subnetwork, making changes in application availability costly and time-consuming. Another disadvantage is the cost and complexity of maintaining a separate subnet and multiple computer systems as hosts for the system.

Accordingly, it is an object of the present invention to provide a security system for connecting a private computer network to another private or public computer network which provides full availability of services to the computer networks while maintaining the private computer network secure from unauthorized access by crackers from the public computer network or other private computer network.

Another object of the present invention is to provide a security system which can be constructed of available standard hardware and software components without requiring costly special coding or hardware.

Another object of the invention is to provide a security system contained entirely within one unit and controllable therefrom.

A further object of the present invention is to provide a security system which protects Unix and MVS hosts connected to the private computer network from unauthorized access by private network users connected to the private local area network (LAN) or wide area network (WAN).

A still further object of the present invention is to provide a security system having two computer motherboards for backing up critical network communication information from one computer motherboard to the other.

Still another object of the invention is to provide the use of unrestricted TCP/IP addresses in a private network which are not limited to the registration procedures of the public Internet, thereby allowing domain names, subnetwork masks, and TCP/IP network/host name addresses to be determined independently in the private networks.

Another object of the present invention is to provide a communication link between a first and second computer network in which the subnetwork mask which is used for communication inside the first computer network is established independently from the subnetwork mask which is presented at the interface to the second network.

SUMMARY OF INVENTION

These and other objects of the present invention are accordingly provided by a security device for preventing unauthorized communications between first computer network and a second computer network. We have discovered that internetwork security can be achieved by providing a security system which includes a first network motherboard and a second network motherboard with each motherboard having a network interface adapter for communicating with the first and second computer networks, respectively. Each network motherboard also has a transfer adapter for transferring communications received at its own network interface adapter to a transfer adapter on the other network motherboard. The transfer adapters must be matched and identical. All of the necessary hardware and software to implement this security system is readily available from multiple sources and no special hardware or software need be designed to implement this system.

Communications received by the network interface adapters connected to the first and second computer network motherboards in Transmission Control Protocol/Internet Control Protocol (TCP/IP) format or Internet Protocol encapsulated in Internet Packet Exchange, IP(IPX), are translated into Internet Packet Exchange (IPX) format communications for further transmission to the network motherboard connected to the other public or private computer network, respectively. This translation process removes the upper TCP protocol layer, the subnetwork mask and prevents the original IP datagram header containing IP header information, an IP destination address, and an IP source address from being further transmitted to the other network. Routing services: IP packet forwarding, and the TCP/IP layers Routing Information Protocol (RIP), Address Resolution Protocol (ARP) and Internet Control Message Protocol (ICMP) are disabled from being transmitted between the network interface adapter and the transfer adapter of each network motherboard. Removal of the original IP datagram headers and disabling of routing services inhibits an unauthorized user of the first or second computer network from obtaining the IP addresses and the corresponding physical addresses which are necessary for direct communication with nodes on the other network.

The second network motherboard further provides API shim software, and client/server software for permitting communication services to and from the second computer network by requesting nodes of the first network. Alternatively, Dynamic Link Library software can be used in place of, or in addition to API shim software for permitting such communications.

The second network motherboard further sets up a domain name, IP address, and a subnetwork mask to allow users of the second network to find and connect to the second network motherboard. The domain name, IP address, and subnetwork mask are independent from the original domain name, IP address and subnetwork mask which were used at the network interface adapter into the first network motherboard. The independence of the subnetwork masks permits a private network linked to the security system of the present invention to contain as many nodes as desired independently of the subnetwork mask which is presented to the public network side by the second network motherboard.

DETAILED DESCRIPTION OF THE PREFERRED EMBODIMENT

Figure 1:
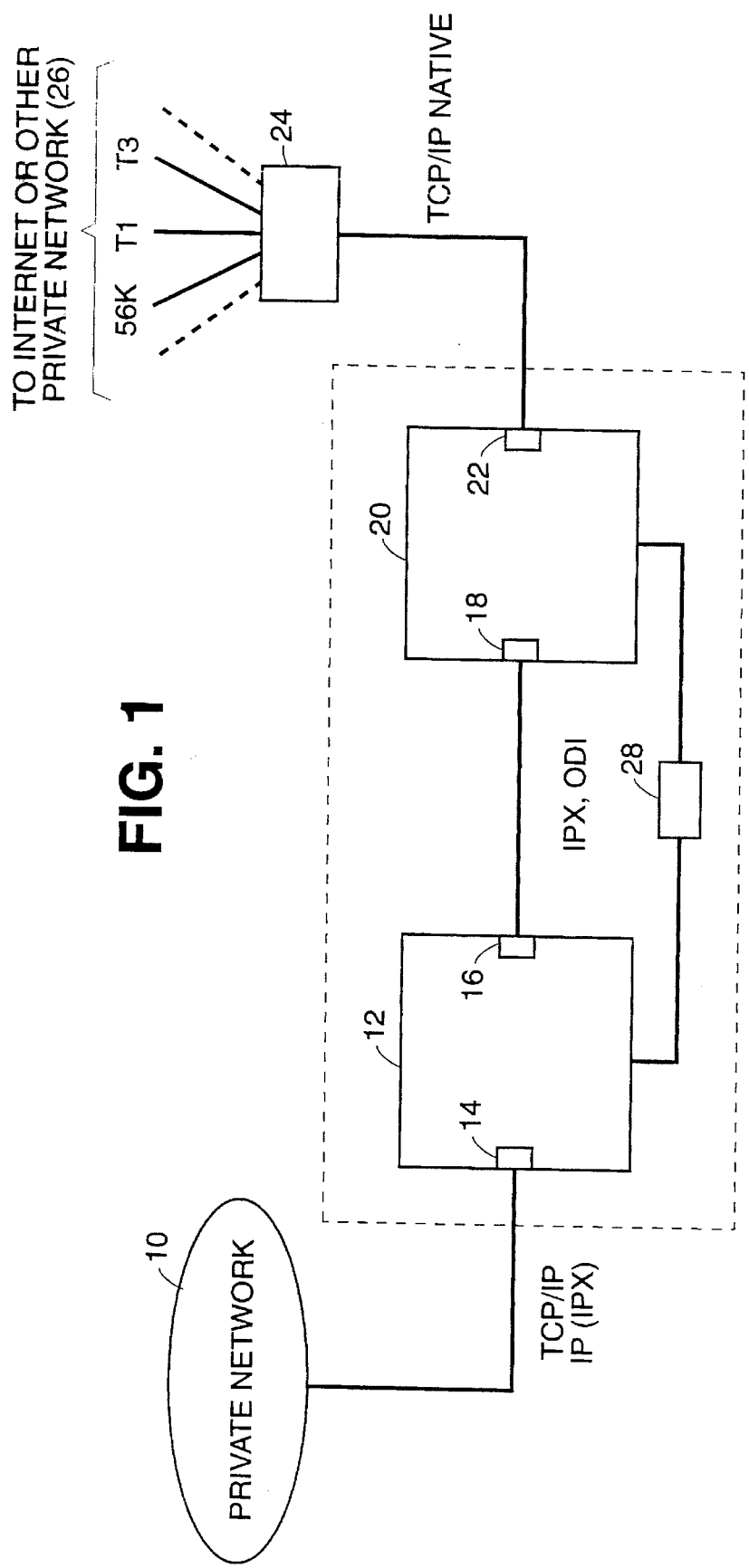
FIG. 1 shows a block diagram of the security system of the present invention and its connection to private and public Internet computer networks.

An embodiment of the present invention is shown in FIG. 1. In FIG. 1 two motherboards 12 and 20 are shown sharing a common power supply 28. Motherboard 20 is connected to a public network, e.g. Internet, 26, while motherboard 12 is connected to a private network 10. Alternatively, motherboard 20 can be connected to another private computer network, 26 e.g. at another branch of the same company. In addition, multiple private and/or public networks can be interconnected in accordance with the invention. Each public or private network is a set of interconnected nodes, the nodes being any common addressable or connectable devices, which can be computers, e.g. workstations, file servers, Unix or MVS mainframes or other digital devices, e.g. routers, printers, controllers, peripherals etc.

Motherboards 12, 20 each have a pair of network adapters 14, 16 and 18, 22, respectively. Network adapters 14 and 22 are network interface adapters used to receive and transmit communications to and from private and public networks 10 and 26, respectively. Network adapters 16 and 18 are transfer adapters used to communicate between motherboards 12 and 20. Transfer adapters 16 and 18 can be any Ethernet type or ARCnet type cards, so long as they are identical and matched. Transfer adapters 16 and 18 cannot reside on the same motherboard.

Each motherboard has standard components such as a microprocessor, a hard disk, a random access memory, preferably 32 MB RAM or higher, ROMBIOS, and a video card. Further, each motherboard has its own separate network operating software, which may be, for example, Novell Netware (R) or Microsoft NT (TM). The use of two motherboards 12 and 20 in conjunction with each other reduces congestion, CPU usage and isolates the private and public networks. Alternatively, the two motherboards can be separate free-standing computer systems which contain at minimum the components described for motherboards 12 and 20, except for common power supply 28.

Network interface adapter 22 of motherboard 20 is preferably a token-ring card which connects through router 24 to common access provider lines 56K, T1 or T3 or to other such lines (indicated by dashed lines) to the Internet 26 or other private network. The software used to bind network interface adapter 22 to the Internet or other private network provides Domain Name Server information, an Internet TCP/IP address, and a subnetwork mask that allows public network users to find and attach to the front end of the security system. For example, Novell Netware (R) Version 3.12 or 4.X and Novell Netware IP (R) or Microsoft NT 3.5+ (TM) can be utilized to establish a native (distinct) TCP/IP connection to the Internet. The network operating software provides services of User Datagram Protocol (UDP) and Transmission Control Protocol (TCP) for communications to and from the Internet or other private network 26. UDP provides an connectionless delivery service to send and receive packets from specific processes between sending and receiving nodes of the Internet. TCP adds reliable stream delivery in addition to the Internet Protocol's connectionless packet delivery service.

The network interface adapter 14 of motherboard 12 may be a token-ring card, an Ethernet Card, or an ARCnet card which connects to the private network 10, which may be either a local area network (LAN) or wide area network (WAN). The software which binds network interface adapter 14 to the private network 10 provides Transmission Control Protocol/Internet Protocol (TCP/IP) services or IP tunnel/ encapsulated IPX IP(IPX) services for communication with private network 10. Appropriate network software for network interface adapter 14 can be Novell Netware (R) Multiprotocol Router (MPR) software or Novell Netware (R) Version 3.12 or 4.x used in conjunction with Novell Netware IP (R). Alternatively, other software file server packages such as Microsoft Windows NTAS 3.5+ can be used. Such software provides a Domain Name Server, a TCP/IP address, and a subnetwork mask which are independent and distinct from the Domain Name Server, TCP/IP address and subnetwork mask used by the network interface adapter on the public side motherboard 20 and which also allows private network users to find and attach to motherboard 20 of the public network side.

Communications received by network interface adapter 14 from private network 10 in Transmission Control Protocol/Internet Control Protocol (TCP/IP) format or IP tunnel/ encapsulated IPX format IP(IPX) are translated into Internet Packet Exchange (IPX) communications for transmission by transfer adapter 16 to transfer adapter 18 of motherboard 20 on the public network side. Likewise, communications received by network interface adapter 22 from public network 26 in Transmission Control Protocol/Internet Control Protocol (TCP/IP) format are also translated into Internet Packet Exchange (IPX) communications for transmission by transfer adapter 18 to transfer adapter 16 of motherboard 12 on the private network side. Translation into IPX format removes the upper TCP protocol layer, and the original IP datagram headers which contain header information, source IP address and destination IP address information from the communications transferred between the network interface adapters and the transfer adapters on each motherboard.

Binding commands provided by the network operating software on each motherboard are used to disable all routing services such as Address Resolution Protocol (ARP), Routing Information Protocol (RIP) and Internet Control Message Protocol (ICMP) between network interface adapters 14, 22 and transfer adapters 16 and 18, respectively. Removal of the IP datagram headers and disabling the routing services inhibits transmission of the physical addresses (also known as "Media Access Control" addresses for use with Ethernet cards) of devices connected to the private network.

Preferably, the network operating software used by network interface adapter 22 on public network motherboard 20 provides the ability to identify each user entering motherboard 20 with a node address specific to the user's physical location and/or the node address of the computer being used to attach. When Ethernet cards are used for the transfer adapters, this information would be preserved. Use of the Ethernet cards would allow use of a node address as another security feature to inhibit multiple private network users from accessing motherboard 20 from other than their specific workstations. However, when ARCnet cards are used as the transfer adapters this function would not be available as the node address information would not be preserved.

Application program interface shims (API shims) or Dynamic Link Libraries (DLL's) are used to permit users from private network 10 to link to motherboard 20 for further communication with the Internet. API shims and DLL's provide an alternative mechanism for passing executable code between the private network device known as a client workstation to motherboard 20 which functions as a server for applications or files communicating with the Internet. Use of commercial API shims and DLL's such as Winsock Complaint Version 1.1x (TM) series and the IPX ODI connection between the transfer adapters 16 and 18 allows transfer of executable code required to execute the applications from motherboard 20.

In addition to the API shim or DLL used to pass executable code to motherboard 20, further client/server software is used such as NCSA Mosaic (TM), Cornell University CELLO (TM), Ameritech/NOTIS WINGOPHER (TM), Pegasus EMAIL (TM) to provide Internet services to private network users by the public network motherboard 20. This allows users on the private network to use full Internet services such as the emulation protocols Telnet, Telnet 3270, Telnet 5250, and the transfer protocols HTTP, FTP, TFTP, anonymous FTP, SMTP, and POP3, to view the public Internet. However, such client/server software on motherboard 20 would not permit the unauthorized private network user on a LAN or WAN to access Unix (R), or MVS (R) or VM (R) mainframe hosts on the private network because higher level emulation services such as Telnet which are necessary to access them are disabled between transfer adapters 16 and 18.

Preferably, additional software is provided on motherboard 20 which includes virus screening and examination software; password software, which identifies potential holes in network security by scanning user and supervisor accounts for known weak passwords and allows encryption; auto logout software for inactive workstations; security and access auditing software, which allows auditing of specific users and workstations as well as directory and file access on the public network side, and also provides encryption between similarly configured security services on user workstations. Preferably, software that allows simultaneous encryption and nonencryption sessions such as PGP would also be installed on motherboard 20.

For interconnection of multiple private or public computer networks a security system according to the present invention should be provided at the interface between each pair of computer networks. For example, when three computer networks are to be interconnected, a security system as embodied in FIG. 1 can be placed between private network 10 and each of the second and third computer networks.

An example of how the present invention can be used to direct communications between the private network and the public Internet while preventing public Internet users from obtaining critical addressing information necessary to communicate directly with workstations of the private network is as follows. Network interface adapter 14 of private network motherboard 12 receives a communication in TCP/IP format from a workstation on the private network 10 requesting Internet access services. Internet access services such as Telnet emulation protocols, file transfer protocols such as FTP, TFTP, and E-mail services, e.g. SMTP are provided by motherboard 20 to workstations connected to the private network through an API shim or DLL which is callable by motherboard 12 through the interface between transfer adapters 16 and 18.

The outgoing communication has an IP source address which identifies the workstation which originated the communication and an IP destination address which identifies network interface adapter 14. The communication is translated into Internet Packet Exchange (IPX) format for transmission to the transfer adapter 16 on motherboard 12 for further transmission to transfer adapter 18 of public network motherboard 20. Translation of the communication into IPX format removes the original IP source and destination addresses from the communication. In addition, all routing services such as ARP, RIP and ICMP are disabled between the two motherboards, preventing the transmission of routing updates which link IP addresses of workstations connected to the private network with their corresponding physical addresses. In this way, the outgoing communication from the private network does not provide addressing information which would enable public Internet users to communicate directly with workstations on the private network.

Motherboard 20 receives the IPX communication through transfer adapter 18 and retranslates it into a TCP/IP format communication having a TCP/IP source address, a subnetwork mask and a Domain Name which identifies network interface adapter 22 as the origin of the communication. The communication, prior to exiting motherboard 20, must pass through additional security software, e.g. password control, or security and access software. The communication is then transmitted to the Internet network and the response is awaited by motherboard 20. When a response is received, motherboard 20 translates the response from TCP/IP format back into IPX format and transmits it through transfer adapter 18 to transfer adapter 16 back to motherboard 12. Motherboard 12 further translates the response back into TCP/IP format for communication back to private network 10. The original IP source and destination addresses from the public network response are likewise removed in this translation process. Routing services are also disabled for inbound communications, thus preventing the transmission of routing updates which link IP addresses of devices connected to the public network with their corresponding physical addresses. Thus, the inbound communication from the public network does not provide addressing information to enable private network users to communicate directly with workstations on the private network. In this way, private network users are also prevented from obtaining addressing information for devices connected to the public network which would enable direct communication with them for the unauthorized exporting of data from the private network.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

What is claimed is:

1. A security system for preventing unauthorized communications between a first network of computers interconnected for Internet Protocol (IP) communications and a second network of computers interconnected for IP communications, while permitting application level communication services between computers connected to said first and said second networks, comprising:

a first network motherboard and a second network motherboard, said first and second network motherboards each having a network interface adapter for communication with said first and said second networks of computers, and for establishing a distinct subnetwork mask, respectively;

each of said network motherboards further having a transfer adapter for communication with said transfer adapter of said other network motherboard, said transfer adapters being identical and matched, each of said network motherboards having network operating software to assign a source address for IP protcol communication in accordance with a susbnetwork mask established for one of said network motherboards which is different from the subnetwork mask established for the other of said network motherboards, said network operating software further including protocol conversion software to translate communications received by each said network interface adapter from said first or said second networks of computers, repectively, in IP protocol format to non-IP protocol format for transmission between the transfer adapters of said first and said second network motherboards, whereby upper level layer protocol information and originating source and destination address information are removed from said communication and routing services communications from said first and second computer networks are prevented from being passed between said network interface adapter and said transfer adapter of each said network motherboard, and thence preventing unauthorized communications between computers connected to said first and said second computer networks; and at least one of said network motherboards having application programming interface (API) shim software for providing application level communication services to the computers connected to said at least one network motherboard notwithstanding the removal of said original source and destination address information, and the preventing of said routing services communications.

2. The security system of claim 1 wherein said second computer network is public, and said second network motherboard has API shim software for providing application level communication services to the computers connected to said network interface adapter of said second network motherboard.

3. The security system of claim 1 wherein each of said first and said second computer networks are private, and each of said network motherboards have API shim software for providing application level communication services to the computers connected to said network interface adapter of each said network motherboard.

4. The security system of claim 1 wherein each of said network motherboards are located within a common unit and share a common power supply.

5. The security system of claim 1 wherein each of said network motherboards includes a magnetic storage device and means for periodically backing up information from each said magnetic storage device to each other said magnetic storage device.

6. The security system of claim 5 wherein said magnetic storage devices are of equal capacity.

7. The security system of claim 1 wherein each of said network motherboards independently establishes a distinct Domain Name.

8. The security system of claim 7 wherein each of said network motherboards independently establishes a distinct transport layer protocol TCP/IP address.

9. The security system in accordance with claim 1 wherein said application programing interface (API) shim software includes dynamic link library (DLL) software.

10. A method of preventing unauthorized communications between a first network of computers interconnected for Internet Protocol (IP) communications and a second network of computers interconnected for IP communications, while permitting application level communication services between computers connected to said first and said second networks, comprising the steps of:

receiving, at a first motherboard from a first network of computers, a communication in IP protocol format;

translating said communication into non-IP protocol format, whereby original source and destination address information are removed from said communication and routing services communications from said first computer network are prevented;

providing application programming interface (API) shim software to permit application level communications between said first and said second networks of computers, notwithstanding the removal of said original source and destination address information, and the preventing of said routing services communications;

transmitting said communication to a second motherboard;

retranslating, at said second motherboard, said communication into IP protocol format and assigning a source address to said communication in accordance with a subnetwork mask established by said second motherboard which is different from the subnetwork mask established for the IP protocol format communication as received by said first motherboard;

transmitting said retranslated communication to said second computer network;

whereby application level communications are permitted between computers connected to said first and said second computer networks, while users connected to said first or said second computer networks are prevented from obtaining routing services information and original source and destination address information pertaining to communications between computers connected to said first and said second computer networks, and thence unauthorized communications between computers connected to said first and said second computer networks are prevented.

11. The method of claim 10 further including the step of controlling, at said second network motherboard, access to said second computer network by devices connected to said first network motherboard.

12. A security interconnection module for use in combination with a second interconnection module for providing application level communication services between a first network of computers interconnected for Internet Protocol (IP) communications and a second network of computers interconnected for IP communications, while preventing unauthorized communications between computers of said first and second networks, comprising:

a network motherboard connected to said first network, said second interconnection module being connected for communication with said second network, said network motherboard including a network interface adapter for communication with said first network of computers, and for establishing a subnetwork mask distinct from the subnetwork mask established by said second interconnection module;

a first transfer adapter for communication with a second transfer adapter included in said second interconnection module, said first transfer adapter and said second transfer adapter being a matched pair;

said network motherboard having network operating software to assign a source address for IP protocol communication in accordance with a subnetwork mask established for said network motherboard which is different from the subnetwork mask established for said other network motherboard, said network operating software further including protocol conversion software to translate communications received from said first network by said network interface adapter from IP protocol format to non-IP protocol format for transmission to said second transfer adapter, thereby removing upper level layer protocol information, originating source and destination address information from said communication and routing services communications are prevented from being transmitted by said first transfer adapter to said second transfer adapter, and thence unauthorized communications between computers connected to said first and said second computer networks; and said network motherboard having application programming interface (API shim) software for providing application level communication services between the computers of said first and said second networks notwithstanding the removal of said original source and destination address information, and the preventing of said routing services communications.

13. The security interconnection module in accordance with claim 12 wherein said application programming interface (API) shim software includes Dynamic Link Library (DLL) software.

* * * * *